(12) United States Patent
Macina

(10) Patent No.: US 6,962,779 B1
(45) Date of Patent: Nov. 8, 2005

(54) METHOD OF DIAGNOSING, MONITORING, STAGING, IMAGING AND TREATING GASTROINTESTINAL CANCERS

(75) Inventor: Roberto A. Macina, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/806,311

(22) PCT Filed: Sep. 30, 1999

(86) PCT No.: PCT/US99/22725

§ 371 (c)(1),
(2), (4) Date: Jul. 18, 2001

(87) PCT Pub. No.: WO00/20640

PCT Pub. Date: Apr. 13, 2000

Related U.S. Application Data

(60) Provisional application No. 60/102,879, filed on Oct. 2, 1998.

(51) Int. Cl.[7] .................................................. C12Q 1/68
(52) U.S. Cl. ......................... 435/6; 435/7; 530/388.85
(58) Field of Search .............................. 435/7.1, 7.92, 435/6; 530/387.1, 387.3, 388.8, 388.85; 536/23.1

(56) References Cited

U.S. PATENT DOCUMENTS

| | | | |
|---|---|---|---|
| 5,601,990 A | | 2/1997 | Wladman |
| 5,731,159 A | | 3/1998 | Wladman |
| 5,861,494 A | * | 1/1999 | Soppet et al. ............... 536/23.1 |
| 5,928,873 A | | 7/1999 | Wladman |
| 6,060,037 A | | 5/2000 | Wladman |
| 6,080,722 A | | 6/2000 | Soppet et al. |
| 6,265,157 B1 | | 7/2001 | Prockop et al. |

FOREIGN PATENT DOCUMENTS

| | | | |
|---|---|---|---|
| JP | 2001025389 A2 | | 1/2001 |
| WO | WO 96/39541 | * | 12/1996 |
| WO | WO 98/11217 A2 | | 3/1998 |
| WO | WO 98/16640 | | 4/1998 |
| WO | WO 00/12758 A1 | | 3/2000 |
| WO | WO 00/20640 A1 | | 4/2000 |
| WO | WO 00/37643 A2 | | 6/2000 |
| WO | WO 01/22920 A2 | | 4/2001 |
| WO | WO 01/32927 A2 | | 5/2001 |
| WO | WO 01/49716 A2 | | 7/2001 |

OTHER PUBLICATIONS

Fu et al (EMBO Journal, 1996, vol. 15, pp. 4392–4401.*
Powell et al (Pharmacogenesis, 1998, vol. 8, pp. 411–421, abstract.*
Vallejo et al (Biochimie, 2000, vol. 82, pp. 1129–1133, abstract.*
Jang et al (Clinical and Experimental Metastasis, 1997, vol. 15, pp. 469–483, abstract.*
Pennica et al (PNAS 95:14717–22, 1998.*
Tascilar et al. (Annals of Oncology 10, Suppl. 4:S107–S110, 1999.*
Tockman et al. (Cancer Research 52:2711s–2718s, 1992.*
Hartupee et al., Isolation and characterization of a cDNA encoding a novel member of a the human regenerating protein family: Reg IV. Biochem. Biophy. Acta. 2001; vol. 1518:287–293.
Database Genebank, Accession No. AY007243, Hartupee et al., *Homo sapiens* regenerating gene type IV mRNA, complete cds., Apr. 23, 2001, see sequence.
Database Genebank, Accession No. XM_034668, NCBI Annotation Project., *Homo sapiens* regenerating gene type IV (REG–IV), mRNA., Aug. 27, 2001, see sequence.
Database Genebank, Accession No. NM_032044, Hartupee et al., *Homo sapiens* regenerating gene type IV (REG–IV), mRNA., May 15, 2001, see sequence.
Database Genebank, Accession No. AF254415, Lin, W.–C., *Homo sapiens* gastrointestinal secretory protein GISP mRNA, complete cds., May 1, 2001, see sequence.
Database Genebank, Accession No. AF345934, Violette et al., *Homo sapiens* regenerating gene type IV, mRNA., Jun. 6, 2001, see sequence.
Database Genebank, Accession No. NP_114433, Hartupee et al., regenerating gene type IV [*Homo sapiens*], May 15, 2001, see sequence.

* cited by examiner

*Primary Examiner*—Larry R. Helms
(74) *Attorney, Agent, or Firm*—Licata & Tyrrell P.C.; Nathan P. Letts

(57) ABSTRACT

The present invention provides a new method for detecting, diagnosing, monitoring, staging, prognosticating, imaging and treating gastointestinal cancers including small intestine, colon and stomach cancer.

6 Claims, No Drawings

METHOD OF DIAGNOSING, MONITORING, STAGING, IMAGING AND TREATING GASTROINTESTINAL CANCERS

This patent application is the U.S. National Stage of International Application PCT/US99/22725, filed Sep. 30, 1999 which claims the benefit of priority from U.S. Provisional Application Ser. No. 60/102,879, filed Oct. 2, 1998.

FIELD OF THE INVENTION

This invention relates, in part, to newly developed assays for detecting, diagnosing, monitoring, staging prognosticating, imaging and treating cancers, particularly gastrointestinal cancers including cancer of the stomach, small intestine and colon.

BACKGROUND OF THE INVENTION

Cancer of the colon is the second most frequently diagnosed malignancy in the United States, as well as the second most common cause of cancer death. Colon cancer is a highly treatable and often curable disease when localized to the bowel. Surgery is the primary treatment and results in cure in approximately 50% of patients. However, recurrence and metastases following surgery is a major problem and often is the ultimate cause of death.

Due to its proximity, cancer of the colon often metastasizes to the small intestine. The prognosis of the cancer spreading to the small intestine is related to the degree of penetration of the tumor through the bowel wall and the presence or absence of nodal involvement. These two characteristics form the basis for all staging systems developed for colon cancer. Various characteristics also assist in prognosticating colon cancer and its spread to the small intestines. For example, bowel obstruction and bowel perforation are indicators of poor prognosis. Elevated pretreatment serum levels of carcinoembryonic antigen (CEA) and of carbohydrate antigen 19-9 (CA 19-9) also have a negative prognostic significance. However, age greater than 70 years at presentation is not a contraindication to standard therapies; acceptable morbidity and mortality, as well as long-term survival, are achieved in this patient population.

Cancer cells can also originate in the small intestine. However, this is a much rarer type of cancer.

Symptoms of cancer of the small intestine typically include pain or cramps in the middle of the abdomen, weight loss without dieting, a lump in the abdomen or blood in the stool.

Cancer of the stomach, also referred to as gastric cancer, also frequently metastasizes to the small intestine due to its proximity. This cancer is often difficult to diagnose in early stages and can be in the stomach for a long time, growing to a large size before symptoms arise. In the early stages of cancer of the stomach, an individual may experience indigestion and stomach discomfort, a bloated feeling after eating, mild nausea, loss of appetite or heartburn. In more advanced stages of stomach cancer, there may be blood in the stool, vomiting, weight loss or more severe pain.

Because of the frequency of these types of cancer (approximately 160,000 new cases of colon and rectal cancer per year alone), the identification of high-risk groups, the demonstrated slow growth of primary lesions and the better survival of early-stage lesions, screening for gastrointestinal cancers should be a part of routine care for all adults starting at age 50, especially those with first-degree relatives with colorectal cancer.

Procedures used for detecting, diagnosing, monitoring, staging, and prognosticating cancer of the colon, small intestine or stomach are of critical importance to the outcome of the patient. Patients diagnosed with early stage cancer generally have a much greater five-year survival rate as compared to the survival rate for patients diagnosed with distant metastasized cancers. New diagnostic methods which are more sensitive and specific for detecting early cancer of the stomach, small intestine and colon are clearly needed.

Patients with gastrointestinal cancers are closely monitored following initial therapy and during adjuvant therapy to determine response to therapy and to detect persistent or recurrent disease of metastasis. There is clearly a need for a cancer marker which is more sensitive and specific in detecting recurrence of these types of cancer.

Another important step in managing gastrointestinal cancers is to determine the stage of the patient's disease. Stage determination has potential prognostic value and provides criteria for designing optimal therapy. Generally, pathological staging of cancer is preferable over clinical staging because the former gives a more accurate prognosis. However, clinical staging would be preferred were it at least as accurate as pathological staging because it does not depend on an invasive procedure to obtain tissue for pathological evaluation. Staging of gastrointestinal cancers would be improved by identifying new markers in cells, tissues, or bodily fluids which could differentiate between different stages of invasion.

Thirteen colon specific genes and naturally occurring variants thereof, referred to as CSG1-13, are disclosed in U.S. Pat. No. 5,733,748 and WO 96/39541 for use as diagnostic markers in colon cancer. Some of these genes and polypeptides encoded thereby are also taught to be useful in determining if the colon cancer has metastasized.

U.S. Pat. No. 5,861,494, which issued January 19, 1999, also discloses a gene and polypeptide encoded thereby for use as a diagnostic marker for colon cancer and as an agent for determining if the colon cancer has metastasized. This gene and the polypeptide encoded thereby are similar in sequence to the cancer specific gene referred to herein as CC2.

It has now been found that CC2 is a useful diagnostic and metastatic marker not only for colon cancer but also for cancer of the stomach and small intestine. Thus, in the present invention, methods are provided for detecting, diagnosing, monitoring, staging, prognosticating, imaging and treating gastrointestinal cancers including cancer of the stomach, small intestine and colon via the cancer specific gene referred to herein as CC2. CC2 refers, among other things, to native protein expressed by the gene comprising the polynucleotide sequence of SEQ ID NO:1. The amino acid sequence of a polypeptide encoded by SEQ ID NO:1 is depicted herein as SEQ ID NO:2. In the alternative, what is meant by CC2 as used herein, means the native mRNA encoded by the gene comprising the polynucleotide sequence of SEQ ID NO:1 or levels of the gene comprising the polynucleotide sequence of SEQ ID NO:1.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of a gastrointestinal cancer by analyzing for changes in levels of CC2 in cells, tissues or bodily fluids compared with levels of CC2 in preferably the same cells, tissues, or bodily fluid type of a normal human control, wherein a change in levels of CC2 in the patient versus the normal human control is associated with a gastrointestinal cancer.

Further provided is a method of diagnosing metastatic cancer in a patient having a gastrointestinal cancer which is not known to have metastasized by identifying a human patient suspected of having a gastrointestinal cancer that has metastasized; analyzing a sample of cells, tissues, or bodily fluid from such patient for CC2; comparing the CC2 levels in such cells, tissues, or bodily fluid with levels of CC2 in preferably the same cells, tissues, or bodily fluid type of a normal human control, wherein an increase in CC2 levels in the patient versus the normal human control is associated with a gastrointestinal cancer which has metastasized.

Also provided by the invention is a method of staging a gastrointestinal cancer in a human which has such cancer by identifying a human patient having such cancer; analyzing a sample of cells, tissues, or bodily fluid from such patient for CC2; comparing CC2 levels in such cells, tissues, or bodily fluid with levels of CC2 in preferably the same cells, tissues, or bodily fluid type of a normal human control sample, wherein an increase in CC2 levels in the patient versus the normal human control is associated with a cancer which is progressing and a decrease in the levels of CC2 is associated with a cancer which is regressing or in remission.

Further provided is a method of monitoring a gastrointestinal cancer in a human having such cancer for the onset of metastasis. The method comprises identifying a human patient having such cancer that is not known to have metastasized; periodically analyzing a sample of cells, tissues, or bodily fluid from such patient for CC2; comparing the CC2 levels in such cells, tissue, or bodily fluid with levels of CC2 in preferably the same cells, tissues, or bodily fluid type of a normal human control sample, wherein an increase in CC2 levels in the patient versus the normal human control is associated with a cancer which has metastasized.

Further provided is a method of monitoring the change in stage of a gastrointestinal cancer in a human having such cancer by looking at levels of CC2 in a human having such cancer. The method comprises identifying a human patient having such cancer; periodically analyzing a sample of cells, tissues, or bodily fluid from such patient for CC2; comparing the CC2 levels in such cells, tissue, or bodily fluid with levels of CC2 in preferably the same cells, tissues, or bodily fluid type of a normal human control sample, wherein an increase in CC2 levels in the patient versus the normal human control is associated with a cancer which is progressing and a decrease in the levels of CC2 is associated with a cancer which is regressing or in remission.

Further provided are antibodies targeted against CC2 or fragments of such antibodies which can be used to detect or image localization of CC2 in a patient for the purpose of detecting or diagnosing a disease or condition. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. These antibodies or fragments thereof can also be used as therapeutic agents in the treatment of diseases characterized by expression of CC2. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating cancers by comparing levels of CC2 with those of CC2 in a normal human control. What is meant by levels of CC2 as used herein, means levels of the native protein expressed by the gene comprising the polynucleotide sequence of SEQ ID NO:1. The amino acid sequence of a polypeptide encoded by SEQ ID NO:1 is depicted herein as SEQ ID NO:2. In the alternative, what is meant by levels of CC2 as used herein, means levels of the native mRNA encoded by the gene comprising the polynucleotide sequence of SEQ ID NO:1 or levels of the gene comprising the polynucleotide sequence of SEQ ID NO:1. Such levels are preferably measured in at least one of cells, tissues and/or bodily fluids, including determination of normal and abnormal levels. Thus, for instance, a diagnostic assay in accordance with the invention for diagnosing overexpression of CC2 protein compared to normal control bodily fluids, cells, or tissue samples may be used to diagnose the presence of cancers, and in particular gastrointestinal cancers. By gastrointestinal cancers it is meant to include stomach cancer, cancer of the small intestine, and colon cancer.

All the methods of the present invention may optionally include measuring levels of other cancer markers as well as CC2. Other cancer markers, in addition to CC2, useful in the present invention will depend on the cancer being tested and are known to those of skill in the art.

Diagnostic Assays

The present invention provides methods for diagnosing the presence of a gastrointestinal cancer by analyzing for changes in levels of CC2 in cells, tissues or bodily fluids compared with levels of CC2 in cells, tissues or bodily fluids of preferably the same type from a normal human control, wherein a change in levels of CC2 in the patient versus the normal human control is associated with the presence of a gastrointestinal cancer.

Without limiting the instant invention, typically, for a quantitative diagnostic assay a positive result indicating the patient being tested has cancer is one in which cells, tissues or bodily fluid levels of the cancer marker, such as CC2, are at least two times higher, and most preferably are at least five times higher, than in preferably the same cells, tissues or bodily fluid of a normal human control.

The present invention also provides a method of diagnosing the onset of metastatic gastrointestinal cancers in a patient having a gastrointestinal cancer which has not yet metastasized. In the method of the present invention, a human cancer patient suspected of having a gastrointestinal cancer which may have metastasized (but which was not previously known to have metastasized) is identified. This is accomplished by a variety of means known to those of skill in the art.

In the present invention, determining the presence of CC2 levels in cells, tissues or bodily fluid, is particularly useful for discriminating between gastrointestinal cancers which have not metastasized and gastrointestinal cancers which have metastasized. Existing techniques have difficulty discriminating between gastrointestinal cancers which have metastasized and gastrointestinal cancers which have not metastasized. However, proper treatment selection is often dependent upon such knowledge.

In the present invention, the cancer marker level measured in cells, tissues or bodily fluid of a human patient is CC2. The measured CC2 level in the human patient is compared with levels of CC2 in preferably the same cells, tissue or bodily fluid type of a normal human control. That is, if the cancer marker being observed is CC2 in serum, this level is preferably compared with the level of CC2 in serum of a normal human control. An increase in the CC2 in the patient versus the normal human control is associated with a gastrointestinal cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CC2, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have a gastrointestinal cancer which has not metastasized.

Staging

The invention also provides a method of staging gastrointestinal cancers in a human patient. The method comprises identifying a human patient having such cancer and analyzing a sample of cells, tissues or bodily fluid from such human patient for CC2. In this method CC2 levels in such cells, tissues or bodily fluid are then compared with levels of CC2 in preferably the same cells, tissues or bodily fluid type of a normal human control sample, wherein an increase in CC2 levels in the human patient versus the normal human control is associated with a cancer which is progressing and a decrease in the levels of CC2 is associated with a cancer which is regressing or in remission.

Monitoring

Further provided is a method of monitoring gastrointestinal cancers in a human having such cancer for the onset of metastasis. The method comprises identifying a human patient having such cancer that is not known to have metastasized; periodically analyzing a sample of cells, tissues or bodily fluid from such human patient for CC2; comparing the CC2 levels in such cells, tissues or bodily fluid with levels of CC2 in preferably the same cells, tissues or bodily fluid type of a normal human control, wherein an increase in CC2 levels in the human patient versus the normal human control is associated with a cancer which has metastasized.

Further provided by this invention is a method of monitoring the change in stage of gastrointestinal cancers in a human having such cancer. The method comprises identifying a human patient having such cancer; periodically analyzing a sample of cells, tissues or bodily fluid from such human patient for CC2; and comparing the CC2 levels in such cells, tissues or bodily fluid with levels of CC2 in preferably the same cells, tissues or bodily fluid type of a normal human control, wherein an increase in CC2 levels in the human patient versus the normal human control is associated with a cancer which is progressing in stage and a decrease in the levels of CC2 is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression (including protein levels), such as CC2 of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to CC2, preferably a monoclonal antibody. In addition a reporter antibody generally is prepared which binds specifically to CC2. The reporter antibody is attached to a detectable reagent such as radioactive, fluorescent or enzymatic reagent, for example horseradish peroxidase enzyme or alkaline phosphatase.

To carry out the ELISA, antibody specific to CC2 is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CC2 binds to the specific antibody attached to the polystyrene dish. Unbound sample is washed out with buffer. A reporter antibody specifically directed to CC2 and linked to horseradish peroxidase is placed in the dish resulting in binding of the reporter antibody to any monoclonal antibody bound to CC2. Unattached reporter antibody is then washed out. Reagents for peroxidase activity, including a calorimetric substrate are then added to the dish. Immobilized peroxidase, linked to CC2 antibodies, produces a colored reaction product. The amount of color developed in a given time period is proportional to the amount of CC2 protein present in the sample. Quantitative results typically are obtained by reference to a standard curve.

A competition assay can also be employed wherein antibodies specific to CC2 are attached to a solid support and labeled CC2 and a sample derived from the host are passed over the solid support. The amount of label detected which is attached to the solid support can be correlated to a quantity of CC2 in the sample.

Nucleic acid methods can also be used to detect CC2 mRNA as a marker for gastrointestinal cancers. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (CDNA) with use of the enzyme reverse transcriptase; the CDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to detect both the expression of and quantitate the level of expression of a gene. In this approach, a cDNA encoding the CC2 gene is fixed to a substrate. The substrate may be of any suitable type including but not limited to glass, nitrocellulose, nylon or plastic. At least a portion of the DNA encoding the CC2 gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts (homogenates or solubilized tissue) obtained from a patient including those from tissue biopsies and autopsy material. Bodily fluids useful in the present invention include blood, urine, saliva or any other bodily secretion or derivative thereof. Blood can include whole blood, plasma, serum or any derivative of blood.

In Vivo Antibody Use

Antibodies which specifically bind to CC2 can also be used in vivo in patients suspected of suffering from gastrointestinal cancers including stomach cancer, cancer of the small intestine, and colon cancer. Specifically, antibodies which specifically bind a CC2 can be injected into a patient suspected of having a gastrointestinal cancer for diagnostic and/or therapeutic purposes. The preparation and use of antibodies for in vivo diagnosis is well known in the art. For example, antibody-chelators labeled with Indium-ill have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against CC2 can be used in a similar manner. Labeled antibodies which specifically bind CC2 can be injected into patients suspected of having a gastrointestinal cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT) . Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with a gastrointestinal cancer, injection of an antibody which specifically binds CC2 can also have a therapeutic benefit. The antibody may exert its therapeutic effect alone. Alternatively, the antibody may be conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648. Yttrium-90 labeled monoclonal antibodies have been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against CC2.

Antibodies which can be used in these in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

The present invention is further described by the following examples. These examples are provided solely to illustrate the invention by reference to specific embodiments. These exemplifications, while illustrating certain aspects of the invention, do not portray the limitations or circumscribe the scope of the disclosed invention.

EXAMPLES

The examples were carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream 3' quencher dye. During PCR, the 5'- 3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control was used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calculate relative quantitation between all the samples studied, the target RNA levels for one sample were used as the basis for comparative results (calibrator). Quantitation relative to the calibrator is obtained using the standard curve method or the comparative method (User Bulletin #2: ABI PRISM 7700 Sequence Detection System).

To evaluate the tissue distribution, and the level of CC2 in normal and tumor tissue, total RNA was extracted from normal tissues, tumor tissues, and from tumors and the corresponding matched normal tissues. Subsequently, first strand cDNA was prepared with reverse transcriptase and the polymerase chain reaction was done using primers and Taqman probe specific to CC2. The results were analyzed using the ABI PRISM 7700 Sequence Detector and are provided in the following table. The absolute numbers are relative-levels of expression of CC2 compared to the kidney (calibrator).

The absolute numbers depicted in Table 1 are relative levels of expression of CC2 in 12 normal different tissues. All the values are compared to normal kidney (calibrator) These RNA samples are commercially available pools, originated by pooling samples of a particular tissue from different individuals.

TABLE 1

Relative Levels of CC2 Expression in Pooled Samples

| Tissue | NORMAL |
|---|---|
| Colon-Ascending | 536 |
| Endometrium | 0 |
| Kidney | 1 |
| Liver | 10 |
| Ovary | 4 |
| Pancreas | 22 |
| Prostate | 332 |
| Small Intestine | 2539 |
| Spleen | 0.0 |
| Stomach | 2062 |
| Testis | 112 |
| Uterus | 2 |

The relative levels of expression in Table 1 show that the higher level of expression of CC2 mRNA is in tissues from the gastrointestinal tract, small intestine (2539), stomach (2062), and colon (536), with a lower level of expression in prostate (332), and testis (112). These results establish that CC2 mRNA expression is highly specific-for gastrointestinal tissues including not only the colon but also the small intestine and stomach.

The absolute numbers in Table 1 were obtained analyzing pools of samples of a particular tissue from different individuals. They should not be compared to the absolute numbers originated from RNA obtained from tissue samples of single individuals depicted in Table 2.

The absolute numbers depicted in Table 2 are relative levels of expression of CC2 in 78 pairs of matching samples. All the values are compared to normal kidney (calibrator). A matching pair is formed by mRNA from the cancer sample for a particular tissue and mRNA from the normal adjacent sample for that same tissue from the shame individual.

TABLE 2

Relative Levels of CC2 Expression in Pooled Samples

| Sample ID | Tissue | Cancer Tissue | Normal Adjacent Tissue |
|---|---|---|---|
| StoAC93 | Stomach 1 | 64860 | 279026 |
| Sto728 | Stomach 2 | 0 | 40 |
| Sto758S | Stomach 3 | 21029 | 2903 |
| Sto915S | Stomach 4 | 3488 | 56 |
| StoAC99 | Stomach 5 | 1162 | 330 |
| Sto115S | Stomach 6 | 404 | 146 |
| Sto15S | Stomach 7 | 4636 | 14 |
| Sto17S | Stomach 8 | 59662 | 538 |
| Sto261S | Stomach 9 | 53061 | 8977 |
| Sto264S | Stomach 10 | 27492 | 84643 |
| Sto27S | Stomach 11 | 20784 | 61 |
| Sto288S | Stomach 12 | 0 | 67 |
| Sto531S | Stomach 13 | 53192 | 8847 |
| Sto539S | Stomach 14 | 1492 | 27 |
| Sto542S | Stomach 15 | 26382 | 425 |
| Sto610S | Stomach 16 | 1029 | 20 |
| Sto88S | Stomach 17 | 3846 | 12 |
| StoAc44 | Stomach 18 | 1.7 | 78 |
| StoMT54 | Stomach 19 | 971 | 67 |
| StoTA73 | Stomach 20 | 35653 | 6020 |
| SmI21XA | Small Intestine 1 | 31016 | 10022 |
| SmIH89 | Small Intestine 2 | 645 | 2227 |
| ClnB56 | Colon-Cecum 1 | 6816 | 971 |
| ClnAS45 | Colon-Ascending 2 | 8757 | 5501 |
| ClnCM67 | Colon-Cecum 3 | 2394 | 578 |
| ClnAS67 | Colon-Ascending 4 | 1566 | 1198 |
| ClnAS43 | Colon-Ascending 5 | 127934 | 923 |
| ClnAS46 | Colon-Ascending 6 | 96620 | 3316 |
| ClnAS98 | Colon Ascending 7 | 83822 | 392 |
| ClnAS89 | Colon-Ascending 8 | 10231 | 4 |
| ClnTX01 | Colon-Transverse 9 | 92 | 331 |
| ClnTX89 | Colon-Transverse 10 | 11114 | 17 |
| ClnTX67 | Colon-Transverse 11 | 683 | 189 |
| ClnMT38 | Colon-Splenic flexture 12 | 0 | 6230 |
| ClnSG89 | Colon-Sigmoid 13 | 2557 | 1243 |
| ClnSG67 | Colon-Sigmoid 14 | 39 | 132 |
| ClnSG33 | Colon-Sigmoid 15 | 17080 | 118542 |
| ClnSG45 | Colon-Sigmoid 16 | 243 | 80 |
| ClnB34 | Colon-Rectosigmoid 17 | 130 | 11 |
| ClnCXGA | Colon-Rectum 18 | 790 | 47152 |
| ClnRC67 | Colon-Rectum 19 | 724 | 419 |
| ClnC9XR | Colon-Rectosigmoid 20 | 425 | 113 |
| ClnRS45 | Colon-Rectosigmoid 21 | 42202 | 1117 |
| ClnRC01 | Colon-Rectum 22 | 2693 | 99 |
| ClnRC89 | Colon-Rectum 23 | 0 | 2402 |
| Bld46XK | Bladder 1 | 0 | 0 |
| Bld66X | Bladder 2 | 15 | 4 |
| Bld32XK | Bladder 3 | 8.5 | 0.4 |
| Kid126XD | Kidney 1 | 5 | 5 |
| Kid12XD | Kidney 2 | 2 | 0 |
| Kid5XD | Kidney 3 | 3.7 | 0.8 |

TABLE 2-continued

Relative Levels of CC2 Expression in Pooled Samples

| Sample ID | Tissue | Cancer Tissue | Normal Adjacent Tissue |
|---|---|---|---|
| Kid6XD | Kidney 4 | 4.3 | 0 |
| Kid106XD | Kidney 5 | 0 | 0.8 |
| Liv42X | Liver 1 | 2 | 1 |
| Liv15XA | Liver 2 | 0.2 | 0.7 |
| Liv94XA | Liver 3 | 0 | 1.4 |
| LngAC69 | Lung 1 | 2 | 0 |
| LngBR94 | Lung 2 | 3 | 0 |
| Lng47XQ | Lung 3 | 0 | 0 |
| Mam59X | Mammary Gland 1 | 0 | 0 |
| MamB011X | Mammary Gland 2 | 0 | 0 |
| MamA06X | Mammary Gland 3 | 15 | 20 |
| Ovr103X | Ovary 1 | 4 | 0 |
| Ovr130X | Ovary 2 | 3 | 3 |
| Pan71XL | Pancreas 1 | 69458 | 15147 |
| Pan82XP | Pancreas 2 | 0 | 0 |
| Pan77X | Pancreas 3 | 0 | 0 |
| Pan92X | Pancreas 4 | 4696 | 52 |
| PanC044 | Pancreas 5 | 34 | 0 |
| Pro12B | Prostate 1 | 21 | 2 |
| Pro23B | Prostate 2 | 23 | 6 |
| Pro13XB | Prostate 3 | 6 | 23 |
| Pro34B | Prostate 4 | 152 | 75 |
| Pro20XB | Prostate 5 | 112 | 13 |
| Pro65XB | Prostate 6 | 60 | 683 |
| Tst39X | Testis 1 | 2361 | 17 |
| Endo10479 | Endometrium 1 | 32 | 0 |
| Utr85XU | Uterus 1 | 0 | 0 |

0 = Negative

In the analysis of matching samples, the higher levels of expression for CC2 are in stomach, small intestine, and colon. This pattern shows a high degree of specificity for gastrointestinal tissues including, not only the colon, but also the stomach and small intestine. These results confirm the tissue specificity results obtained with the panel of normal pooled samples (shown in Table 1).

The level of mRNA expression in cancer samples and the isogenic normal adjacent tissue from the same individual were also compared. This comparison provides an indication of specificity for the cancer stage (e.g. different levels of mRNA expression in the cancer sample compared to the normal adjacent tissue). Table 2 shows overexpression of CC2 in 15 primary stomach cancer tissues compared with their respective normal adjacent (stomach samples #3, 4, 5, 6, 7, 8, 9, 11, 13, 14, 15, 16, 17, 19, and 20). There is overexpression in the cancer tissues for 75% of the stomach matching samples tested (total of 20 stomach matching samples).

CC2 is also differentially expressed in the two tested matching samples for cancer of the small intestine. Sample #1 shows upregulation for the mRNA of CC2 in cancer, whereas sample #2, shows lower expression in cancer.

CC2 is differentially expressed in twenty-three matching samples for colon cancer. Samples #1, 2, 3, 4, 5, 6, 7, 8, 10, 11, 13, 16, 17, 19, 20, 21 and 22 show upregulation for the mRNA of CC2 in cancer, whereas samples #9, 12, 14, 15, 18, and 23 show lower expression in the cancer sample when compared to the normal adjacent tissue.

Altogether, the high level of tissue specificity for gastrointestinal tissues, plus the mRNA differential expression in several of the primary stomach, small intestine, and colon matching samples tested indicate CC2 to be a diagnostic marker for gastrointestinal cancers including not only colon cancer, but also stomach cancer and cancer of the small intestine.

What is claimed is:

1. A method for detecting the presence of cancer of the stomach or small intestine in a patient comprising:
   (a) measuring levels of CC2 in cells, tissues or bodily fluids from a patient; and
   (b) comparing the measured levels of CC2 with levels of CC2 in cells, tissues or bodily fluids from a normal human control sample of the same, type of cells, tissues or bodily fluids as the patient, wherein an increase in measured levels of CC2 in said patient versus normal human control sample of the same type of cells, tissues or bodily fluids as the patient is associated with the presence of cancer of the stomach or small intestine, wherein CC2 comprises SEQ ID NO:1 or SEQ ID NO:2.

2. The method of claim 1 wherein the CC2 comprises SEQ ID NO:1.

3. The method of claim 1 wherein the CC2 comprises SEQ ID NO:2.

4. The method of claim 1 wherein CC2 levels are measured in cells from the patient and normal matched human control sample.

5. The method of claim 1 wherein CC2 levels are measured in tissue from the patient and normal matched human control sample.

6. The method of claim 1 wherein CC2 levels are measured in bodily fluid from the patient and normal matched human control sample.

* * * * *

SEQUENCE LISTING

```
<160> NUMBER OF SEQ ID NOS: 2

<210> SEQ ID NO 1
<211> LENGTH: 1255
<212> TYPE: DNA
<213> ORGANISM: Homo sapien
<220> FEATURE:
<221> NAME/KEY: misc_feature
<222> LOCATION: (1224)..(1224)
<223> OTHER INFORMATION: n= a, c, g or t
<220> FEATURE:
<221> NAME/KEY: misc_feature
<222> LOCATION: (1234)..(1234)
<223> OTHER INFORMATION: n= a, c, g or t
<220> FEATURE:
<221> NAME/KEY: misc_feature
<222> LOCATION: (1238)..(1238)
<223> OTHER INFORMATION: n= a, c, g or t
<220> FEATURE:
<221> NAME/KEY: misc_feature
<222> LOCATION: (1247)..(1248)
<223> OTHER INFORMATION: n= a, c, g or t

<400> SEQUENCE: 1
aagatataaa agctccagaa acgttgactg ggaccactgg aggcacgagg aaggcagggg      60
cccttagagt cttggttgcc aaacagattt gcagatcaag gagaacccag gagtttcaaa     120
gaagcgctag taaggtctct gagatccttg cactagctac atcctcaggg taggaggaag     180
```

-continued

| | |
|---|---|
| atggcttcca gaagcatgcg gctgctccta ttgctgagct gcctggccaa aacaggagtc | 240 |
| ctgggtgata tcatcatgag acccagctgt gctcctggat ggttttacca caagtccaat | 300 |
| tgctatggtt acttcaggaa gctgaggaac tggtctgatg ccgagctcga gtgtcagtct | 360 |
| tacggaaacg gagcccacct ggcatctatc ctgagtttaa aggaagccag caccatagca | 420 |
| gagtacataa gtggctatca gagaagccag ccgatatgga ttggcctgca cgacccacag | 480 |
| aagaggcagc agtggcagtg gattgatggg gccatgtatc tgtacagatc ctggtctggc | 540 |
| aagtccatgg gtgggaacaa gcactgtgct gagatgagct ccaataacaa cttttttaact | 600 |
| tggagcagca acgaatgcaa caagcgccaa cacttcctgt gcaagtaccg accatagagc | 660 |
| aagaatcaag attctgctaa ctcctgcaca gccccgtcct cttcctttct gctagcctgg | 720 |
| ctaaatctgc tcattatttc agaggggaaa cctagcaaac taagagtgat aagggcccta | 780 |
| ctacactggc tttttaggc ttagagacag aaactttagc attggcccag tagtggcttc | 840 |
| tagctctaaa tgtttgcccc gccatccctt ccacagtat ccttcttccc tcctcccctg | 900 |
| tctctggctg tctcgagcag tctagaagag tgcatctcca gcctatgaaa cagctgggtc | 960 |
| tttggccata agaagtaaag atttgaagac agaaggaaga aactcaggag taagcttcta | 1020 |
| gaccccttca gcttctacac ccttctgccc tctctccatt gcctgcaccc caccccagcc | 1080 |
| actcaactcc tgcttgtttt tcctttggcc ataggaaggt ttaccagtag aatccttgct | 1140 |
| aggttgatgt gggccataca ttcctttaat aaaccattgt gtacatgaag aaaaaaaaaa | 1200 |
| aaaaaaaaaa aaaggggggg ccgnttcaag gggntccnaa gtttganntg acggg | 1255 |

<210> SEQ ID NO 2
<211> LENGTH: 153
<212> TYPE: PRT
<213> ORGANISM: Homo sapien

<400> SEQUENCE: 2

```
Met Arg Leu Leu Leu Leu Ser Cys Leu Ala Lys Thr Gly Val Leu
1               5                   10                  15

Gly Asp Ile Ile Met Arg Pro Ser Cys Ala Pro Gly Trp Phe Tyr His
            20                  25                  30

Lys Ser Asn Cys Tyr Gly Tyr Phe Arg Lys Leu Arg Asn Trp Ser Asp
        35                  40                  45

Ala Glu Leu Glu Cys Gln Ser Tyr Gly Asn Gly Ala His Leu Ala Ser
    50                  55                  60

Ile Leu Ser Leu Lys Glu Ala Ser Thr Ile Ala Glu Tyr Ile Ser Gly
65                  70                  75                  80

Tyr Gln Arg Ser Gln Pro Ile Trp Ile Gly Leu His Asp Pro Gln Lys
                85                  90                  95

Arg Gln Gln Trp Gln Trp Ile Asp Gly Ala Met Tyr Leu Tyr Arg Ser
            100                 105                 110

Trp Ser Gly Lys Ser Met Gly Gly Asn Lys His Cys Ala Glu Met Ser
        115                 120                 125

Ser Asn Asn Asn Phe Leu Thr Trp Ser Ser Asn Glu Cys Asn Lys Arg
    130                 135                 140

Gln His Phe Leu Cys Lys Tyr Arg Pro
145                 150
```